(12) United States Patent
Spinelli et al.

(10) Patent No.: US 8,024,040 B2
(45) Date of Patent: *Sep. 20, 2011

(54) METHOD AND SYSTEM FOR TREATMENT OF NEUROCARDIOGENIC SYNCOPE

(75) Inventors: Julio C. Spinelli, Shoreview, MN (US); Qingsheng Zhu, Little Canada, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 883 days.

This patent is subject to a terminal disclaimer.

(21) Appl. No.: 10/862,831

(22) Filed: Jun. 7, 2004

(65) Prior Publication Data
US 2005/0021098 A1    Jan. 27, 2005

Related U.S. Application Data

(63) Continuation of application No. 09/917,259, filed on Jul. 27, 2001, now Pat. No. 6,748,271.

(51) Int. Cl.
*A61N 1/16* (2006.01)
(52) U.S. Cl. .............................. 607/9; 607/7
(58) Field of Classification Search .............. 607/4–5, 607/9, 17, 23, 2, 7, 14, 25, 28
See application file for complete search history.

(56) References Cited

U.S. PATENT DOCUMENTS

| | | |
|---|---|---|
| 3,608,542 A | 9/1971 | Pacela et al. |
| 4,003,379 A | 1/1977 | Ellinwood, Jr. |
| 4,271,192 A | 6/1981 | Wurtman et al. |
| 4,470,987 A | 9/1984 | Wurtman et al. |
| 4,576,183 A | 3/1986 | Plicchi et al. |
| 4,651,716 A | 3/1987 | Forester et al. |
| 4,884,576 A | 12/1989 | Alt |
| 4,987,897 A | 1/1991 | Funke |
| 5,025,786 A | 6/1991 | Siegel |
| 5,113,869 A | 5/1992 | Nappholz et al. |
| 5,117,825 A | 6/1992 | Grevious |
| 5,199,428 A | 4/1993 | Obel et al. |
| 5,213,098 A * | 5/1993 | Bennett et al. ............ 607/18 |
| 5,233,985 A | 8/1993 | Hudrlik |
| 5,246,008 A | 9/1993 | Mueller et al. |
| 5,271,395 A | 12/1993 | Wahlstrand et al. |
| 5,282,840 A | 2/1994 | Hudrlik et al. |
| 5,292,343 A | 3/1994 | Blanchette et al. |

(Continued)

FOREIGN PATENT DOCUMENTS

EP    348271    12/1989

(Continued)

OTHER PUBLICATIONS

Mai, J., et al., "Enhanced Rate Response Algorithm for Orthostatic Compensation Pacing", *PACE*, 23, Naspe Abstracts, Abstract No. 678, (Apr. 2000), 722.

(Continued)

*Primary Examiner* — Niketa I Patel
*Assistant Examiner* — Rex Holmes
(74) *Attorney, Agent, or Firm* — Schwegman, Lundberg & Woessner, P.A.

(57) ABSTRACT

A method and apparatus for treating or preventing neurocardiogenic syncope is disclosed. Upon detection of bradycardia or a drop in blood pressure indicating the onset of syncope, electrostimulation pulses are delivered during the heart's refractory period. The pulses are non-excitatory but increase myocardial contractility and thereby increase cardiac output.

18 Claims, 2 Drawing Sheets

U.S. PATENT DOCUMENTS

| | | | |
|---|---|---|---|
| 5,300,093 A | 4/1994 | Koestner et al. | |
| 5,313,953 A | 5/1994 | Yomtov et al. | |
| 5,324,309 A | 6/1994 | Kallok | |
| 5,324,315 A | 6/1994 | Grevious | |
| 5,344,429 A | 9/1994 | Smits | |
| 5,354,317 A | 10/1994 | Alt | |
| 5,354,319 A | 10/1994 | Wyborny et al. | |
| 5,370,665 A | 12/1994 | Hudrlik | |
| 5,411,031 A | 5/1995 | Yomtov | |
| 5,441,525 A | 8/1995 | Shelton et al. | |
| 5,464,434 A | 11/1995 | Alt | |
| 5,479,369 A | 12/1995 | Matsumura et al. | |
| 5,501,701 A | 3/1996 | Markowitz et al. | |
| 5,507,785 A | 4/1996 | Deno | |
| 5,534,018 A | 7/1996 | Wahlstrand et al. | |
| 5,540,728 A | 7/1996 | Shelton et al. | |
| 5,562,711 A | 10/1996 | Yerich et al. | |
| 5,626,623 A | 5/1997 | Kieval et al. | |
| 5,676,686 A | 10/1997 | Jensen et al. | |
| 5,706,829 A | 1/1998 | Kadri | |
| 5,725,561 A | 3/1998 | Stroebel et al. | |
| 5,725,562 A | 3/1998 | Sheldon | |
| 5,732,710 A | 3/1998 | Rabinovich et al. | |
| 5,749,369 A | 5/1998 | Rabinovich et al. | |
| 5,749,900 A | 5/1998 | Schroeppel et al. | |
| 5,788,643 A | 8/1998 | Feldman | |
| 5,800,464 A | 9/1998 | Kieval | |
| 5,865,760 A | 2/1999 | Lidman et al. | |
| 5,874,420 A | 2/1999 | Pelleg | |
| 5,876,353 A | 3/1999 | Riff | |
| 5,913,879 A | 6/1999 | Ferek-Petric et al. | |
| 5,919,210 A | 7/1999 | Lurie et al. | |
| 5,957,861 A | 9/1999 | Combs et al. | |
| 5,957,957 A | 9/1999 | Sheldon | |
| 6,026,324 A | 2/2000 | Carlson | |
| 6,035,233 A | 3/2000 | Schroeppel et al. | |
| 6,044,297 A | 3/2000 | Sheldon et al. | |
| 6,049,735 A | 4/2000 | Hartley et al. | |
| 6,076,015 A | 6/2000 | Hartley et al. | |
| 6,078,834 A | 6/2000 | Lurie et al. | |
| 6,104,949 A | 8/2000 | Pitts Crick et al. | |
| 6,317,631 B1 | 11/2001 | Ben-Haim et al. | |
| 6,438,408 B1 | 8/2002 | Mulligan et al. | |
| 6,473,640 B1 | 10/2002 | Erlebacher | |
| 6,512,949 B1 | 1/2003 | Combs et al. | |
| 6,625,492 B2 | 9/2003 | Florio et al. | |
| 6,690,971 B2 * | 2/2004 | Schauerte et al. | 607/17 |
| 6,738,667 B2 * | 5/2004 | Deno et al. | 607/23 |
| 6,748,271 B2 | 6/2004 | Spinelli et al. | |
| 6,907,288 B2 | 6/2005 | Daum | |
| 6,912,420 B2 | 6/2005 | Scheiner et al. | |
| 7,191,000 B2 | 3/2007 | Zhu et al. | |
| 7,333,854 B1 | 2/2008 | Brewer et al. | |
| 2002/0115939 A1 | 8/2002 | Mulligan et al. | |
| 2002/0147475 A1 | 10/2002 | Scheiner et al. | |
| 2002/0147476 A1 | 10/2002 | Daum | |
| 2003/0028221 A1 | 2/2003 | Zhu et al. | |
| 2003/0074029 A1 | 4/2003 | Deno et al. | |
| 2003/0191503 A1 | 10/2003 | Zhu et al. | |
| 2004/0049235 A1 | 3/2004 | Deno et al. | |

FOREIGN PATENT DOCUMENTS

| | | |
|---|---|---|
| EP | 0620420 | 10/1994 |
| WO | WO-8400227 | 1/1984 |
| WO | WO-02053026 | 7/2002 |
| WO | WO-02053228 | 7/2002 |
| WO | WO-03020364 | 3/2003 |

OTHER PUBLICATIONS

Petersen, M E., et al., "Cardiac pacing for vasovagal syncope: a reasonable therapeutic option?", *Pacing Clin Electrophysiol.*, 20(3 Pt 2), (Mar. 1997),824-6.

Sra, J S., et al., "Cardiac pacing during neurocardiogenic (vasovagal) syncope", *J Cardiovasc Electrophysiol.*, 6(9), (Sep. 1995),751-60.

Berman, Irwin R, et al., "Transthoracic electrical impedance s a guide to intravascular overload", Archives of Surgery, 102(1), (Jan. 1971), 61-64.

Charach, Gideon, et al., "Transthoracic monitoring of the impedance of the right lung in patients with cardiogenic pulmonary edema", Critical Care Medicine, 29(6), (Jun. 2001), 1137-44.

Ellenbogen, Kenneth A, et al., "Rate-adaptive pacing based on impedance-derived minute ventilation", Clinical Cardiac Pacing, Philadelphia : Saunders, (1995), 219-233.

Kusumoto, Fred M, et al., "Medical Progress: Cardiac Pacing", New England Journal of Medicine, 334(2), (Jan. 11, 1996), 89-98.

Lau, C P, et al., "Rate-responsive pacing with a pacemaker that detects respiratory rate (Biorate): clinical advantages and complications", Clinical Cardiology, 11(5), (May 1988), 318-24.

Luepker, R. V., et al., "Transthoracic Electrical Impedance: Quantitative Evaluation of a Non-Invasive Measure of Thoracic Fluid Volume", American Heart Journal, 85(1), (Jan. 1973), 83-93.

Pomerantz, M, et al., "Transthoracic electrical impedance for the early detection of pulmonary edema", Surgery, 66(1), (Jul. 1969), 260-8.

Shoemaker, William C, et al., "Multicenter trial of a new thoracic electrical bioimpedance device for cardiac output estimation", Critical Care Medicine, 22(12), (Dec. 1994), 1907-1912.

Viirola, H, et al., "Controlled growth of antimony-doped tin dioxide thin films by atomic layer epitaxy", Thin Solid Films, 251, (Nov. 1994), 127-135.

Viirola, H, et al., "Controlled growth of tin dioxide thin films by atomic layer epitaxy", Thin Solid Films, 249(2), (Sep. 1994), 144-149.

Visokay, M R, "Application of HfSiON as a gate dielectric material", Applied Physics Letters, 80(17), (Apr. 2002), 3183-3185.

Wuerz, Richard C, et al., "Effects of prehospital medications on mortality and length of stay in congestive heart failure", Annals of Emergency Medicine, 21(6), (Jun. 1992), 669-74.

Yu, Cheuk-Man, et al., "Early warning of CHF hospitalization by intra-thoracic impedance measurement in CHF patients with pacemakers", Pacing and Clinical Electrophysiology, 24, (Apr. 2001), 19.

* cited by examiner

METHOD AND SYSTEM FOR TREATMENT OF NEUROCARDIOGENIC SYNCOPE

CROSS-REFERENCE TO RELATED APPLICATION(S)

This application is a continuation of U.S. patent application Ser. No. 09/917,259, filed on Jul. 27, 2001, now issued as U.S. Pat. No. 6,748,271, the specification of which is incorporated herein by reference.

FIELD OF THE INVENTION

This invention pertains to implantable medical devices and to methods for treating syncopal episodes.

BACKGROUND

Syncope, or fainting, is a transient loss of consciousness and postural tone that may be due a number of etiologies, both cardiovascular and non-cardiovascular. The most common pathophysiogical basis of syncope is an acute decrease in cerebral blood flow secondary to a decrease in cardiac output, thereby causing cerebral hypoxia. Such a decrease in cardiac output can be due to, for example, cardiac arrhythmias or cardiac outflow obstructions. Neurocardiogenic syncope is a relatively benign condition in which dysfunction of the autonomic nervous system causes an inappropriate slowing of the heart (bradycardia) to result in hypotension. Classic neurogenic syncope (vasovagal syncope) occurs when inappropriate reflex inhibition of the sympathetic nervous system and increased parasympathetic activity causes both bradycardia and peripheral vasodilation. Vasovagal syncope may occur in otherwise healthy individuals and in patients with a variety of underlying diseases. A number of factors may precipitate vasovagal syncope, including a hot or crowded environment, alcohol, extreme fatigue, hunger, chronic recumbency, prolonged standing, and emotional or stressful situations. Another type of neurocardiogenic syncope involves failure of the baroreceptor reflex to transiently increase the heart rate when an individual rises to an upright position, causing venous pooling in the lower extremities and decreased venous return to the right side of the heart.

Even if the cause of the syncope is benign, however, its consequences may not be. Falls during syncope can result in fractures, and episodes that occur while driving can be extremely dangerous. Chronic and recurring syncope can create a level of functional impairment similar to that produced by other chronic debilitating disorders.

SUMMARY OF THE INVENTION

The present invention is a system and method for preventing and/or treating syncope with cardiac electrostimulation delivered by an implantable medical device that increases cardiac output. The heart rate is monitored and, when bradycardia below a specified limit value is detected that indicates the onset of a syncopal episode, electrostimulation pulses are delivered to a ventricle during its refractory period. Such electrostimulation pulses are non-excitatory but serve to increase the contractility of the ventricle. Stroke volume and cardiac output are thereby increased in order to prevent or lessen the severity of the syncopal episode.

DETAILED DESCRIPTION

The present invention for treating neurocardiogenic syncope may be incorporated into various types of cardiac rhythm management devices having means for sensing and electrostimulating the heart. As will be described below, the invention may most conveniently be incorporated into a pacemaker.

1. System Description

Cardiac rhythm management devices are implantable devices that provide electrical stimulation to selected chambers of the heart in order to treat disorders of cardiac rhythm and include pacemakers and implantable cardioverter/defibrillators. A pacemaker is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Pacing therapy may also be applied in order to treat cardiac rhythms that are too fast, termed anti-tachycardia pacing. (As the term is used herein, a pacemaker is any cardiac rhythm management device with a pacing functionality, regardless of any other functions it may perform such as the delivery cardioversion or defibrillation shocks to terminate atrial or ventricular fibrillation.)

Pacemakers are typically implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

Figure 1:
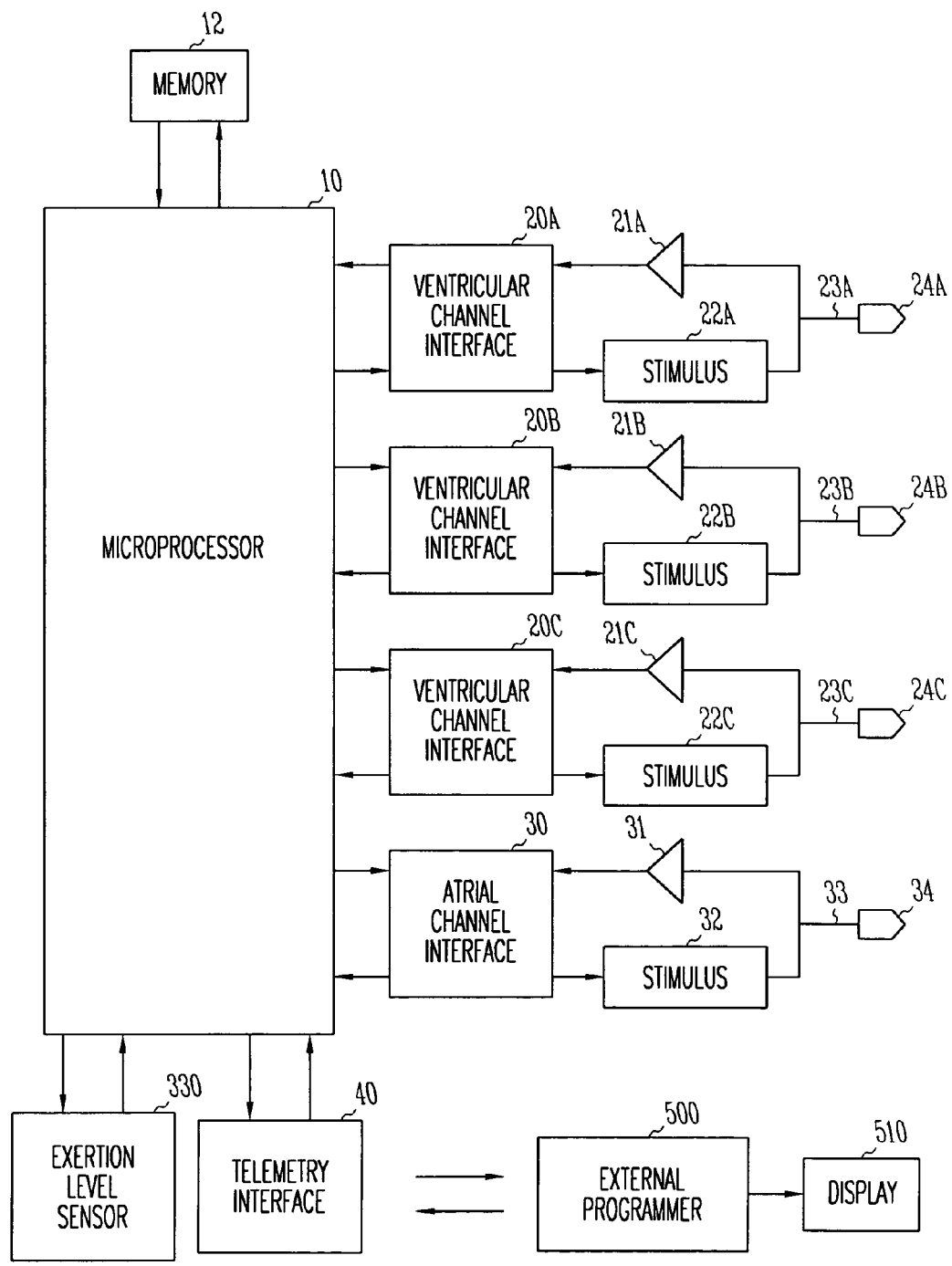
FIG. 1 is a system diagram of an exemplary cardiac rhythm management device.

FIG. 1 shows a system diagram of a microprocessor-based cardiac rhythm management device suitable for delivering various cardiac rhythm management therapies including treatment of neurocardiogenic syncope as detailed below. The device is a pacemaker that is physically configured with sensing and pacing channels for both atria and both ventricles. The controller 10 of the device is a microprocessor that communicates with a memory 12 via a bidirectional data bus. The memory 12 typically comprises a ROM (read-only memory) for program storage and a RAM (random-access memory) for data storage. The pacemaker has an atrial sensing and pacing channel comprising electrode 34, lead 33, sensing amplifiers 31, pulse generators 32, and atrial channel interface 30 which communicates bidirectionally with microprocessor 10. The device also has a plurality of ventricular sensing and pacing/stimulation channels for one or both ventricles, three of which are shown as comprising electrodes 24a-c, leads 23a-c, sensing amplifiers 21a-c, pulse generators 22a-c, and ventricular channel interfaces 20a-c. In this embodiment, a single electrode is used for sensing and pacing in each channel, known as a unipolar lead. Other embodiments may employ bipolar leads that include two electrodes for outputting a pacing pulse and/or sensing intrinsic activity. The channel interfaces 20a-c and 30 may include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. An exertion level sensor 330 (e.g., an accelerometer or a minute ventilation sensor) enables the controller to adapt the pacing rate in accordance with changes in the patient's physical activity. A telemetry interface 40 is also provided for communicating with an external programmer 500 that has an associated display 510.

Bradycardia pacing modes refer to pacing algorithms used to pace the atria and/or ventricles when the intrinsic ventricular rate is inadequate either due to AV conduction blocks or sinus node dysfunction. Such modes may either be single-chamber pacing, where either an atrium or a ventricle is paced, or dual-chamber pacing in which both an atrium and a ventricle are paced. Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

2. Cardiac Contractility Modulation

In accordance with the invention, when bradycardia below a specified threshold that could otherwise cause syncope is detected by the device, one or more electrostimulatory pulses are delivered to the heart during the refractory period of one or more heartbeats. Such stimulation, referred to herein as cardiac contractility modulation (CCM), is non-excitatory because it is delivered during the refractory period of the ventricle. (The refractory period of the ventricle in this case refers to that portion of the ventricle to which is delivered the electrostimulatory pulse being refractory.) It has been found that such stimulation causes an increase in myocardial contractility, presumably by increasing intracellular calcium concentration. The increase in contractility increases stroke volume so that more blood is pumped in a subsequent systolic contraction. The increased stroke volume counteracts the bradycardia and thereby stabilizes cardiac output to either prevent or shorten the duration of a syncopal episode. The invention may be a dedicated implantable device or incorporated into an implantable cardiac rhythm management device such as a pacemaker, implantable cardioverter/defibrillator, or combination device.

Figure 2:
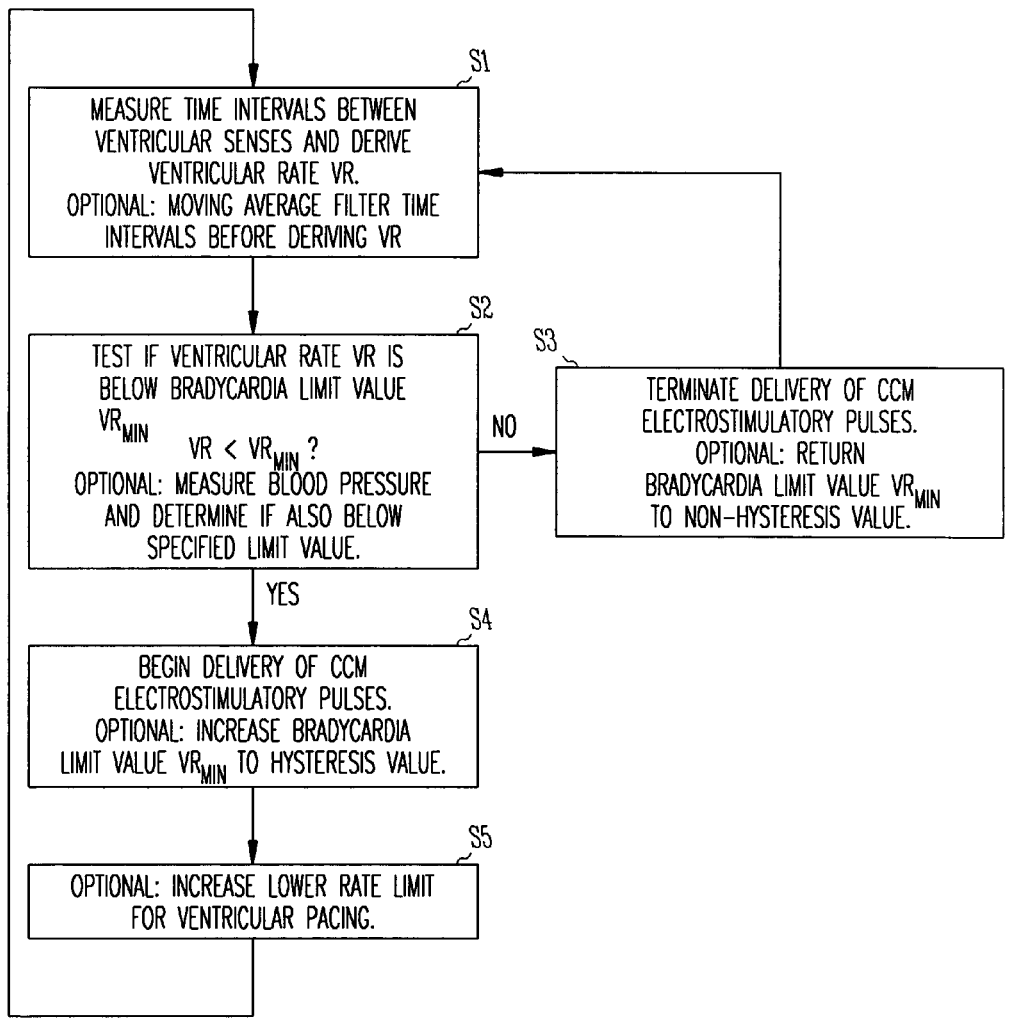
FIG. 2 is a flowchart illustrating an exemplary control scheme for implementing the invention.

Sensing of cardiac activity and delivery of CCM stimulatory pulses may be accomplished using sensing/pacing channels otherwise used for pacing the ventricles with a bradycardia pacing mode or using channels dedicated for the purpose of delivering CCM pulses. In the device shown in FIG. 1, for example, any of the ventricular sensing/pacing channels may be used for delivering CCM stimulation pulses. FIG. 2 illustrates a basic control scheme for carrying out the method as would be implemented by programming the microprocessor 10. In the illustrated scheme, several optional steps are described that may or may not be implemented in various embodiments. At step S1, the ventricular rate is continuously monitored by receiving ventricular senses representing intrinsic ventricular depolarizations from one of the ventricular sensing channels. To derive the ventricular rate VR, the interval between successive ventricular senses is measured and compared to a maximum limit value in order to detect bradycardia as shown at step S2, where the inverse of the interval corresponding to the ventricular rate VR is compared with a bradycardia limit value $VR_{min}$. Bradycardia is detected if $VR<VR_{min}$, and delivery of CCM stimulation pulses is then initiated at step S4 using one of the ventricular stimulation channels. The stimulation pulses are delivered during the refractory period of the ventricle by timing a pulse to occur within a refractory interval following a ventricular sense or a ventricular pace if the device is also operating in a bradycardia pacing mode. The device then returns to the monitoring of the ventricular rate at step S1, and delivery of CCM pulses is terminated at step S3 if the ventricular rate VR equals or exceeds the limit value $VR_{min}$. Optionally, the limit value $VR_{min}$ may be increased to a hysteresis value $VR_{min}$ at step S4 so that CCM pulse delivery is maintained until the heart rate rises above an increased bradycardia limit value. In that case, the bradycardia limit value is returned to a non-hysteresis value at step S3 when CCM pulse delivery is terminated. In another option, if the device is also operating in a bradycardia pacing mode, the lower rate limit may be increased upon detection of bradycardia as shown at step S5. The heart is then paced at a faster rate simultaneously with the application of cardiac contractility modulation.

Modifications may be made to the method so that one or more additional criteria are employed to confirm that a syncopal episode is taking place before CCM stimulatory pulses are delivered. One such modification is shown at step S1 where the measured intervals between ventricular senses are moving average filtered in order to derive the ventricular rate VR. The moving average filter smooths the ventricular rate so that bradycardia is not detected when long intervals occur solely due to the variability of the instantaneous rate. Another optional modification is to measure the blood pressure as shown at step S2 and deliver CCM stimulatory pulses only if it is below a specified limit value. The blood pressure measurement may be used instead of a sensed heart rate decrease or may be used to confirm the rate decrease before initiating therapy. One way of measuring blood pressure in a cardiac rhythm management device is to use an accelerometer, such as the exertion level sensor 330, as described in U.S. Pat. No. 6,026,324, issued to Carlson and hereby incorporated by reference. In a further refinement, the magnitude and/or duration of the CCM pulses can be increased as the measured blood pressure decreases in order to maximize the effectiveness of the therapy.

Cardiac contractility modulation may also be applied to multiple sites in order to distribute the effects of the stimulation pulses. Because this type of non-excitatory stimulation also increases local oxygen consumption, distributing the stimulation over a plurality of sites serves to help prevent potentially deleterious effects at the stimulation sites. Accordingly, at step S5 the ventricular stimulation channels can be alternated with each stimulatory pulse so that the pulses are alternately delivered to electrodes 24a-c.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for operating a cardiac rhythm management device, comprising:
    sensing ventricular depolarizations and generating ventricular sense signals in accordance therewith;
    deriving a ventricular rate as a function of a plurality of time intervals between successive ventricular senses;
    detecting a ventricular bradycardia when the derived ventricular rate is below a specified bradycardia limit value;
    initiating delivery of one or more electrostimulation pulses to the ventricle while the ventricle is refractory when ventricular bradycardia is detected from the derived ventricular rate to thereby increase the contractility of the ventricle, wherein such electrostimulation pulses are timed to occur within a refractory interval following a ventricular sense or pace;
    pacing the ventricle upon expiration of an escape interval without receipt of a ventricular sense, the inverse of the escape interval being the lower rate limit; and,
    increasing the lower rate limit when bradycardia is detected.

2. The method of claim 1 further comprising delivering the electrostimulation pulse within the specified refractory time interval after each ventricular sense when bradycardia is detected.

3. The method of claim 1 further comprising terminating delivery of electrostimulation pulses when the ventricular rate equals or exceeds the bradycardia limit value.

4. The method of claim 3 further comprising increasing the bradycardia limit value to a hysteresis value when delivery of the electrostimulation pulses is begun and returning the bradycardia limit value to its previous non-hysteresis value when delivery of the electrostimulation pulses is terminated.

5. The method of claim 1 further comprising alternating the delivery of the electrostimulation pulses between different stimulation sites of the ventricle.

6. The method of claim 1 further comprising measuring a blood pressure and delivering the electrostimulation pulses only when the measured blood pressure is below a specified minimum value.

7. The method of claim 6 wherein the blood pressure is measured with an accelerometer.

8. The method of claim 6 further comprising adjusting the magnitude of the stimulation pulses in accordance with the measured blood pressure.

9. The method of claim 6 further comprising adjusting the duration of the stimulation pulses in accordance with the measured blood pressure.

10. A cardiac rhythm management device, comprising:
    a sensing amplifier for sensing ventricular depolarizations through a sensing channel and generating ventricular sense signals in accordance therewith;
    a pulse generator for delivering electrostimulation pulses to a ventricle through a stimulation channel;
    a controller for controlling the delivery of stimulation pulses to the ventricle;
    wherein the controller is programmed to derive a ventricular rate as a function of a plurality of time intervals between successive ventricular senses, detect a ventricular bradycardia when the derived ventricular rate is below a specified bradycardia limit value, and initiate delivery of one or more stimulation pulses while the ventricle is refractory when ventricular bradycardia is detected from the derived ventricular rate to thereby increase the contractility of the ventricle, wherein such electrostimulation pulses are timed to occur within a refractory interval following a ventricular sense or pace; and,
    wherein the controller is configured to pace the ventricle upon expiration of an escape interval without receipt of a ventricular sense, the inverse of the escape interval being the lower rate limit, and to increase the lower rate limit when bradycardia is detected.

11. The device of claim 10 wherein the controller is programmed to deliver the electrostimulation pulse within the specified refractory time interval after each ventricular sense when bradycardia is detected.

12. The device of claim 10 wherein the controller is programmed to terminate delivery of electrostimulation pulses when the ventricular rate equals or exceeds the bradycardia limit value.

13. The device of claim 12 further comprising specified hysteresis and non-hysteresis values for the bradycardia limit value and wherein the controller is programmed to increase the bradycardia limit value the hysteresis value when delivery of electrostimulation pulses is begun and return the bradycardia limit value to the non-hysteresis value when delivery of electrostimulation pulses is terminated.

14. The device of claim 10 further comprising a plurality of stimulation channels and wherein the controller is programmed to alternate the delivery of electrostimulation pulses between different stimulation channels.

15. The device of claim 10 further comprising means for measuring blood pressure and wherein the controller is programmed to measure a blood pressure and deliver an electrostimulation pulse only when the measured blood pressure is below a specified minimum value.

16. The device of claim 15 wherein the blood pressure measuring means is an accelerometer.

17. The device of claim 15 wherein the controller is programmed to adjust the magnitude of the stimulation pulses in accordance with the measured blood pressure.

18. The device of claim 15 wherein the controller is programmed to adjust the duration of the stimulation pulses in accordance with the measured blood pressure.

* * * * *